(12) United States Patent
Yangdai et al.

(10) Patent No.: US 11,627,947 B2
(45) Date of Patent: Apr. 18, 2023

(54) SAMPLING CAPSULE AND SAMPLING CAPSULE SYSTEM

(71) Applicant: ANKON TECHNOLOGIES CO., LTD, Wuhan (CN)

(72) Inventors: Tianyi Yangdai, Wuhan (CN); Fanhua Ming, Shanghai (CN)

(73) Assignee: ANKON TECHNOLOGIES CO., LTD, Wuhan (CN)

( * ) Notice: Subject to any disclaimer, the term of this patent is extended or adjusted under 35 U.S.C. 154(b) by 611 days.

(21) Appl. No.: 16/658,069

(22) Filed: Oct. 19, 2019

(65) Prior Publication Data
US 2020/0121303 A1    Apr. 23, 2020

(30) Foreign Application Priority Data
Oct. 19, 2018    (CN) .......................... 201811219936.8

(51) Int. Cl.
*A61B 10/00*    (2006.01)
*A61B 1/04*    (2006.01)

(52) U.S. Cl.
CPC .......... *A61B 10/0045* (2013.01); *A61B 1/041* (2013.01); *A61B 2010/0061* (2013.01); *A61B 2562/162* (2013.01)

(58) Field of Classification Search
CPC ............... A61B 10/0045; A61B 1/041; A61B 2010/0061; A61B 2562/162; A61B 10/04; A61B 5/6861; A61B 90/36; A61B 5/036; A61B 5/038; A61B 5/07; A61B 5/073; A61B 5/42; A61B 5/4839; A61B 2562/0247; A61B 10/02; A61B 10/06; A61B 5/062; A61B 1/00004; A61B 1/00016; A61B 5/0084; A61B 5/053; A61B 5/14539; A61B 5/14546; A61B 1/00097; A61B 1/128
See application file for complete search history.

(56) References Cited

U.S. PATENT DOCUMENTS

| | | | |
|---|---|---|---|
| 10,610,104 B2* | 4/2020 | Pak | A61B 5/4255 |
| 2009/0012503 A1* | 1/2009 | Kawano | F04B 43/06 604/891.1 |
| 2012/0232569 A1* | 9/2012 | Wright | A61B 17/1285 606/158 |
| 2017/0245741 A1* | 8/2017 | Valdastri | A61B 1/015 |

* cited by examiner

*Primary Examiner* — Matthew Kremer
*Assistant Examiner* — Kyle W. Kretzer
(74) *Attorney, Agent, or Firm* — Treasure IP Group, LLC

(57) ABSTRACT

The present invention provides a sampling capsule and a sampling capsule system. The sampling capsule includes an enclosure, a partition wall arranged in the enclosure, and a sample chamber enclosed by the partition wall and the enclosure at a first side of the partition wall. The sampling capsule further includes an inner sample inlet on the partition wall, an outer sample inlet, a sampling tube and a switch assembly. The outer sample inlet is on the enclosure at a second side of the partition wall. The sampling tube connects the outer sample inlet and the inner sample inlet, and the switch assembly clamps or unclamps a portion of the sampling tube. When sampling is needed, the switch assembly unclamps the sampling tube to sample liquid. When sampling ends, the switch assembly tightly clamps the sampling tube to prevent sample liquid leak or contamination.

19 Claims, 3 Drawing Sheets

SAMPLING CAPSULE AND SAMPLING CAPSULE SYSTEM

CROSS-REFERENCE OF RELATED APPLICATIONS

The application claims priority to Chinese Patent Application No. 201811219936.8 filed on Oct. 19, 2018, the contents of which are incorporated by reference herein.

FIELD OF INVENTION

The present invention relates to a medical device, and more particularly to a sampling capsule and sampling capsule system which have high versatility, precisely controlled sampling time and volume, and can prevent sampling liquid leak or contamination.

BACKGROUND

Sampling capsule is an intelligent capsule device employed to sample liquid in gastrointestinal tract. Generally, a sampling capsule comprises a sample chamber, a sampling port and a releasing port connected to the sample chamber. When the sampling capsule reaches a predetermined position inside a patient's GI tract, the sampling port is opened, liquid flows into the sample chamber, and after the sampling capsule is discharged, the sampling liquid in the sample chamber can be taken out from the releasing port for pathological analysis.

An existing sampling capsule has a sampling port made of a material that can be dissolved in a specific environment inside GI tract. When the sampling capsule reaches a desired region of the GI tract, the material is dissolved to form a sampling hole, through which a digestive juice is sucked into the capsule due to pressure difference. However, such sampling capsule is not versatile for all kinds of GI tract environments. In addition, the sampling volume cannot be controlled, and after sampling is finished, the sampling hole cannot be closed, resulting in sampling digestive juice leak or contamination by other liquid.

It is necessary to provide an improved sampling capsule and sampling capsule system to solve the said problem.

SUMMARY OF THE INVENTION

The present invention provides a sampling capsule and sampling capsule system which have high versatility, precisely controlled sampling time and volume, and can prevent sample liquid leak or contamination.

In one embodiment, the present invention provides a sampling capsule comprising an enclosure, a partition wall arranged in the enclosure, a sample chamber enclosed by the partition wall and the enclosure at a first side of the partition wall; and further comprising an inner sample inlet on the partition wall, an outer sample inlet on the enclosure at a second side of the partition wall, a sampling tube connecting the outer sample inlet and the inner sample inlet, and a switch assembly that clamps or unclamps a portion of the sampling tube.

In one embodiment, the switch assembly comprises a clamping mechanism that clamps or unclamps the portion of the sampling tube, and a control unit that communicates with the clamping mechanism.

In one embodiment, the clamping mechanism comprises a pair of clamping arms respectively arranged at two sides of the sampling tube, a shape memory alloy with its two ends respectively connected to the pair of clamping arms to drive the clamping arms move towards or away from each other, and a temperature control element for controlling the temperature of the shape memory alloy, wherein the temperature control element is in communication with the control unit. The shape memory alloy has a first shape state and a distance between the clamping arms is a first distance when temperature is lower than a shape restoration threshold. The shape memory alloy has a second shape state and a distance between the clamping arms is a second distance when the temperature is higher than the shape restoration threshold. The first distance is less than or greater than the second distance, and in the first distance and the second distance, the smaller one is configured for the sampling tube clamped by the clamping arms, and the larger one is configured for the sampling tube unclamped by the clamping arms.

In one embodiment, the temperature control element is a heating element, and the first distance is less than the second distance.

In one embodiment, the temperature control element is a cooling element, and the first distance is greater than the second distance.

In one embodiment, the shape memory alloy is arranged between the pair of clamping arms with two ends respectively connected to two face-to-face sides of the clamping arms, or the shape memory alloy is arranged at the same side of the pair of clamping arms with two ends respectively connected to two reverse sides of the clamping arms by connecting pieces, or the shape memory alloy is arranged at the same side of the pair of clamping arms with two ends respectively connected to the sides of the clamping arms facing the shape memory alloy.

In one embodiment, a pair of clamping arms correspond to a shape memory alloy, or multiple pairs of clamping arms correspond to a shape memory alloy.

In one embodiment, a shape memory alloy corresponds to a temperature control element, or multiple shape memory alloys correspond to a temperature control element.

In one embodiment, the switch assembly further comprises an auxiliary block arranged on the inner wall of the enclosure to limit the pair of clamping arms to move in a straight line.

In one embodiment, the switch assembly further comprises:

a sensor communicating with the control unit, wherein the sensor collects physiological parameters and/or images inside a patient's GI tract, and a storage module communicating with the control unit, wherein the storage module stores the physiological parameters and/or images of different regions of a patient's GI tract when they are normal or have lesions.

In one embodiment, the sensor is selected from an image sensor, a pH sensor, and an ultrasonic sensor, wherein part of the enclosure is transparent when the sampling capsule comprises the image sensor, and the enclosure has a window through which the pH sensor contacts liquid inside GI tract when the sampling capsule comprises the pH sensor.

In one embodiment, the sampling capsule further comprises a wireless transmission module for communicating with an external processing terminal.

In one embodiment, the sampling tube comprises an axial tube and a radial tube when the number of the inner sample inlet is one and the number of the outer sample inlets is at least two, the axial tube extending axially along the sampling capsule and connecting to the inner inlet, and the radial tube extending radially along the sampling capsule and connecting to each of the outer inlets, wherein the axial tube is clamped or unclamped by the switch assembly, or the radial tube is clamped or unclamped by the switch assembly.

In another embodiment, the sampling tube comprises one or more axial tubes and one or more radial tubes when the number of the inner sample inlets is at least two and the number of the outer sample inlets is at least two, the axial tubes extending axially along the sampling capsule and connecting to each of the inner inlets one by one, and the radial tubes extending radially along the sampling capsule and connecting to each of the outer inlets one by one, wherein the axial tubes are clamped or unclamped by the switch assembly, or the radial tubes are clamped or unclamped by the switch assembly.

In still another embodiment, when the number of the inner sample inlets is at least two and the number of the outer sample inlets is at least two, multiple sampling tubes connect all of the inner sample inlets and the outer sample inlets, and each of the sampling tubes connects at least one of the inner sample inlets and at least one of the outer sample inlets.

In one embodiment, the sampling capsule further comprises a releasing port on the enclosure of the first side of the partition wall and being connected to the sample chamber to obtain the sample liquid.

The present invention further provides a sampling capsule system comprising a sampling capsule as described above and an external processing terminal is in communication with the switch assembly.

In one embodiment, the switch assembly comprises a control unit that controls operating state of the switch assembly, and a wireless transmission module that communicates with the control unit, wherein the external processing terminal communicates with the control unit through the wireless transmission module.

The sampling capsule disclosed herein sucks sample liquid into the sample chamber through the outer sample inlet, the sampling tube and the inner sample inlet when the sampling capsule reaches the region of interest inside a patient's GI tract. The switch assembly unclamps the sampling tube allowing liquid to flow through. When sampling ends, the switch assembly tightly clamps the sampling tube make it in a blocked state to prevent sample liquid leak or contamination. The switch assembly can control the unblocking state and time of the sampling tube to precisely control the volume of sample liquid sucked into the sample chamber. In addition, the switch assembly actively controls the unclamping or clamping of the sampling tube to make the sampling capsule free to suck sample liquid at any position inside a GI tract without being affected by a special environment therein. Therefore, the sampling capsule has a high versatility.

DETAILED DESCRIPTION

Figure 1:
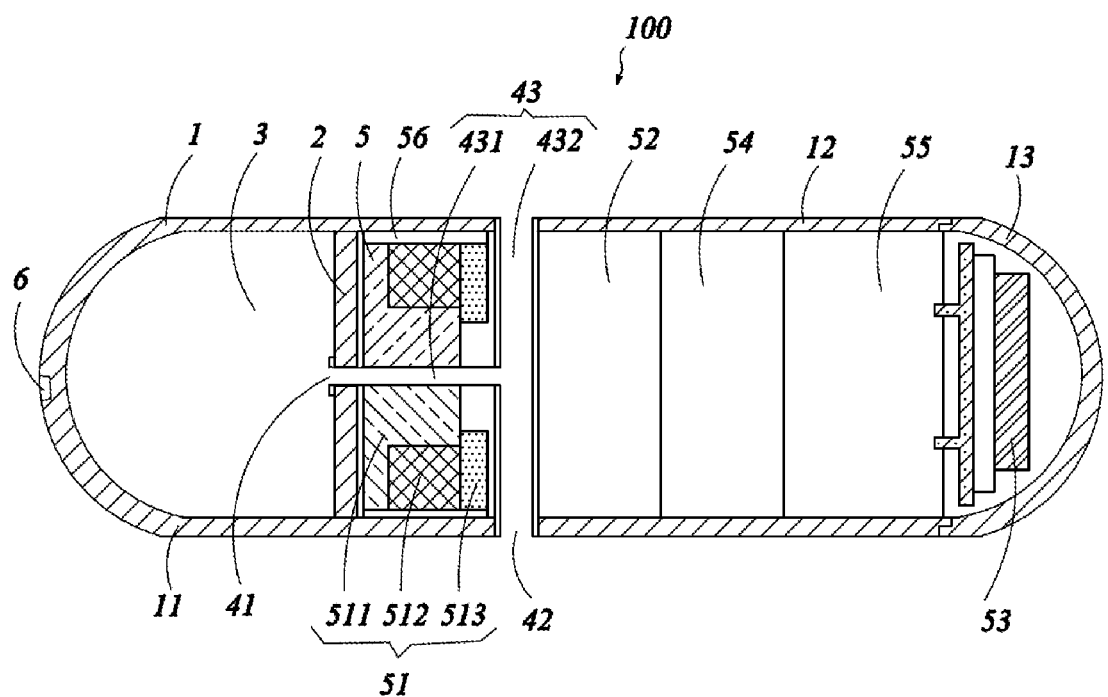
FIG. 1 is a structural view showing one preferred embodiment of a sampling capsule according to the present invention, in which a sampling tube is unclamped.
Figure 2:
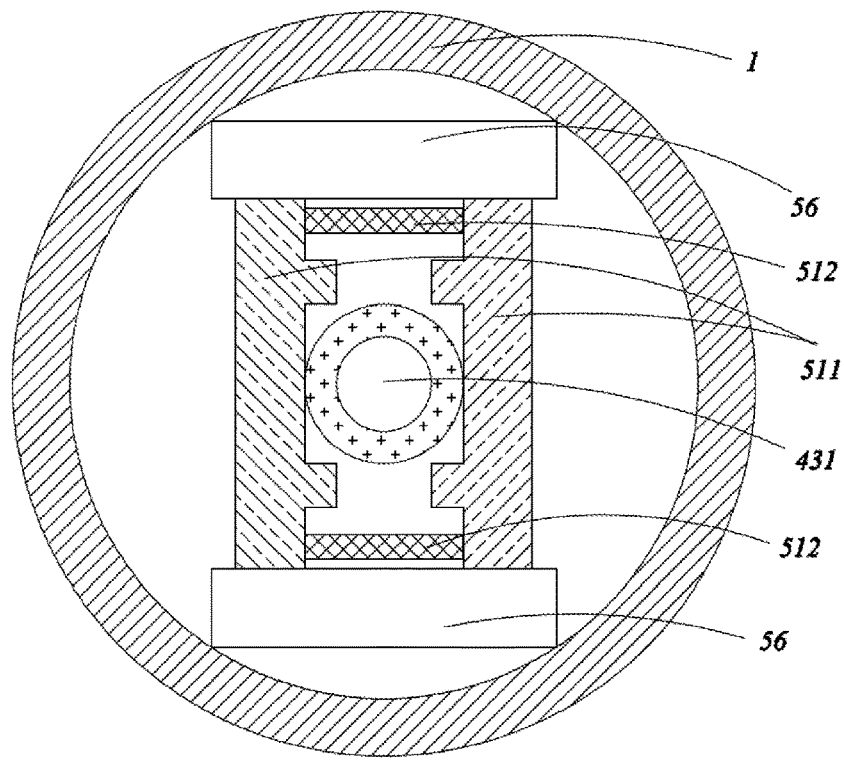
FIG. 2 is a sectional view of the sampling capsule as shown in FIG. 1, in which the sampling tube is unclamped.
Figure 3:
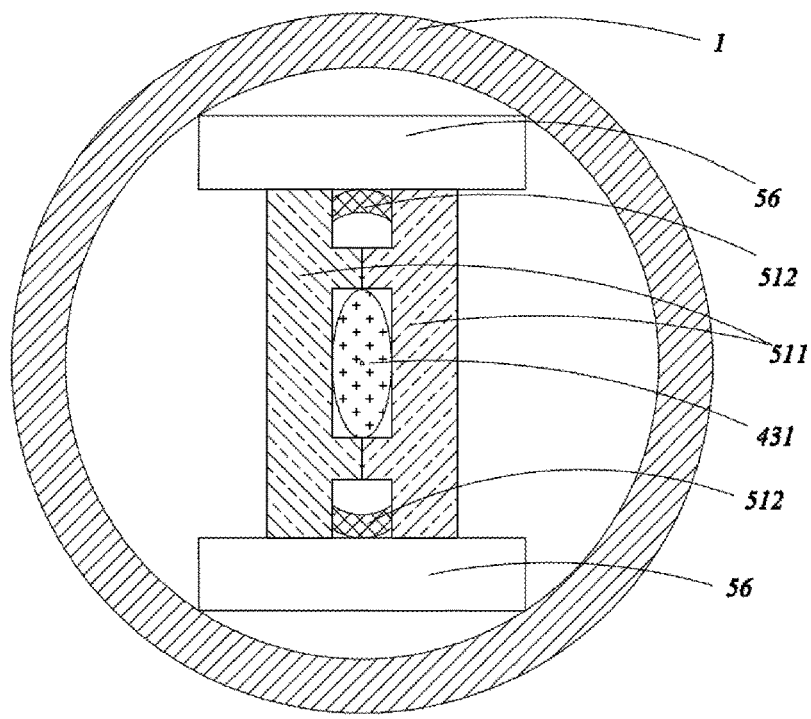
FIG. 3 is a sectional view of the sampling capsule as shown in FIG. 2, in which the sampling tube is clamped.
Figure 4:
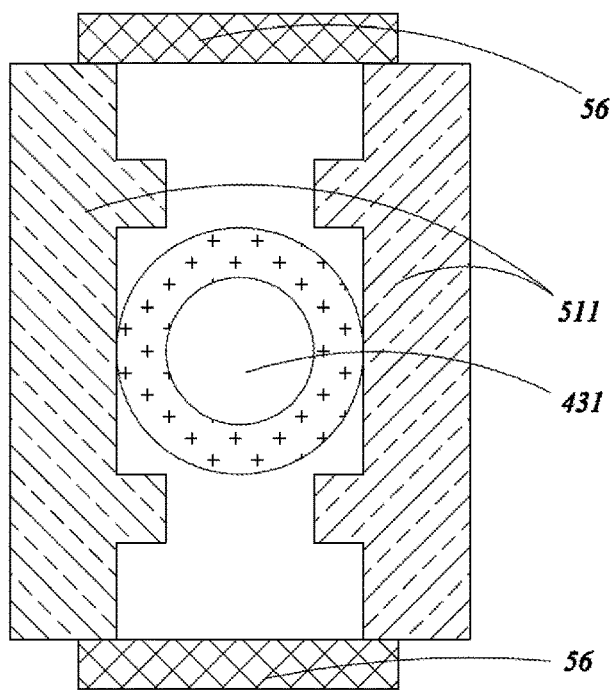
FIG. 4 is a schematic view showing another preferred embodiment of a sampling capsule according to the present invention, in which a shape memory alloy, a pair of clamping arms, and an axial tube which is unclamped are in a cooperative state.
Figure 5:
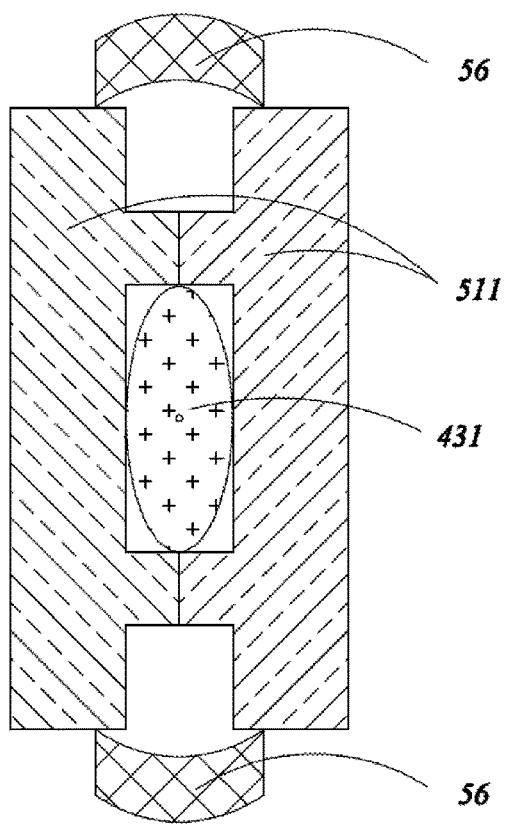
FIG. 5 is a schematic view of the sampling capsule as shown in FIG. 4 when the axial tube is clamped.

The present invention can be described in detail below with reference to the accompanying drawings and preferred embodiments. However, the embodiments are not intended to limit the invention, and the structural, method, or functional changes made by those skilled in the art in accordance with the embodiments are included in the scope of the present invention.

In the figures of the present invention, some sizes of a structure or portion may be exaggerated relative to other structures or portions for ease of illustration, and thus, are merely used to illustrate the basic structure of the subject matter of the present invention.

In addition, the terms representing spatial relative position such as "On", "Above", "Under", "Below", and the like are used herein for ease of illustration to describe the positional relationship of one unit or feature to another unit or feature as shown in the figures. These terms may be intended to show different orientations of a device in use or operation other than the orientations shown in the figures. For example, if the device shown in the figures is turned over, the units or features that are described as "Below" or "Under" other units or features can be "Above" other units or features. Thus, the exemplary term "Below" can encompass two orientations of "Below" and "Above". The device may be oriented (rotated 90 degrees or other orientations) in other ways and the space related descriptors used herein are interpreted accordingly.

Referring to FIGS. 1~5, showing one preferred embodiment of a sampling capsule 100 according to the present invention.

The sampling capsule 100 comprises an enclosure 1, a partition wall 2 arranged in the enclosure 1, a sample chamber 3, an inner sample inlet 41 on the partition wall 2, an outer sample inlet 42, a sampling tube 43 and a switch assembly 5. The sample chamber 3 is enclosed by the partition wall 2 and the enclosure 1 at a first side of the partition wall 2, and the outer sample inlet 42 is on the enclosure 1 at a second side of the partition wall 2. The sampling tube 43 connects the outer sample inlet 42 and the inner sample inlet 41, and the switch assembly 5 clamps or unclamps a portion of the sampling tube 43.

In general, when the sampling capsule 100 is at a desired location of a patient's GI tract or reaches a region having lesion inside a patient's GI tract, liquid sampling is needed. The sampling capsule 100 sucks sample liquid into the sample chamber 3 through the outer sample inlet 42, the sampling tube 43 and the inner sample inlet 41 when the sampling capsule 100 reaches the region of interest inside a patient's GI tract. The switch assembly 5 unclamps the sampling tube 43 allowing liquid to flow through. When sampling ends, the switch assembly 5 tightly clamps the sampling tube 43 in a blocked state to prevent sample liquid leak or contamination. The switch assembly 5 can control the unblocking state and time of the sampling tube 43 to precisely control the volume of sample liquid sucked into the sample chamber. In addition, the switch assembly 5 actively controls the unclamping or clamping of the sampling tube 43 to make the sampling capsule 100 free to suck sample liquid at any position inside a GI tract without being affected by a special environment therein. Therefore, the sampling capsule 100 has a high versatility.

After the sampling capsule 100 is discharged, the methods of taking out the sample liquid includes, but not limited to, unclamping the sampling tube 43 to allow the sample liquid to flow out through the inner sample inlet 41, the sampling tube 43 and the outer sample inlet 42 for pathological analysis. Or the sampling capsule 100 comprises a releasing port 6 on the enclosure 1 on the first side of the partition wall 2 communicating with the sample chamber 3, and the sample chamber 3 is pierced from the releasing port 6 to obtain the sample liquid using a syringe or the like. The releasing port 6 is made of soft material like rubber.

Specifically, the enclosure 1 is made of any material that is harmless to human body and resistant to the corrosion of digestive juice, and the enclosure 1 is designed to have a length of less than 30 mm, such as 27 mm, and a diameter of less than 12 mm, such as 11.6 mm to easily enter any part of a patient's GI tract to sample liquid. Moreover, the enclosure 1 is constructed by at least two parts joined together to facilitate arrangement of internal components. For example, as shown in FIG. 1, the enclosure 1 is composed of a first enclosure 11, a second enclosure 12 and a third enclosure 13 which are distributed along the longitudinal direction of the sampling capsule 100, and the three parts are connected by threads, glue, etc.

The partition wall 2 is designed integrally with the enclosure 1 on the first side of the partition wall 2 to form the sample chamber 3 with a good leak tightness. Or the partition wall 2 and the enclosure 1 on the first side of the partition wall 2 have a split-type design and the tightness at the junction of the two ensures that the sample chamber 3 can maintain its required vacuum degree.

The sample chamber 3 is a vacuum chamber with a capacity of more than 0.3 mL, such as 0.4 mL~0.7 mL, and the vacuum of the chamber can be −90 kPa~−80 kPa to ensure that the volume of sample liquid is greater than 0.3 mL Before use, the sampling tube 43 is unclamped, and a vacuum device is used to pump the air in the sample chamber 3, and when a required vacuum degree is reached, the sampling tube 43 is clamped to maintain the sample chamber 3 at such vacuum degree. In use, when the sampling capsule 100 reaches a desired region of a patient's GI tract, the sampling tube 43 is unclamped to suck sample liquid into the sample chamber 3 due to internal and external pressure difference.

The switch assembly 5 comprises a clamping mechanism 51 that clamps or unclamps a portion of the sampling tube 43, and a control unit 52 that communicates with the clamping mechanism 51.

The clamping mechanism 51 comprises a pair of clamping arms 511, a shape memory alloy 512 and a temperature control element 513. The pair of clamping arms 511 is respectively arranged at two sides of the sampling tube 43. The shape memory alloy 512 with its two ends respectively connects to the pair of clamping arms 511 to drive the clamping arms 511 move towards or away from each other. The temperature control element 513 is used to control the temperature of the shape memory alloy 512, and the temperature control element 513 is in communication with the control unit 52. Through control of the temperature control element 513, the control unit 52 can further control the operating state of the switch assembly 5.

The pair of clamping arms 511 includes two clamping arms 511 disposed separately, which may also be referred to as clamping arm pair 511.

A pair of clamping arms 511 corresponds to a shape memory alloy 512. Or multiple pairs of clamping arms 511 correspond to a shape memory alloy 512, that is a shape memory alloy 512 can drive multiple pairs of clamping arms 511 at the same time. The arrangement of the pair of clamping arms 511 is adjusted according to the arrangement of the sampling tube 43, and the number and arrangement position of the shape memory alloy 512 are adjusted according to the arrangement of the clamping arms 511.

A shape memory alloy 512 corresponds to a temperature control element 513. Or multiple shape memory alloys 512 correspond to a temperature control element 513, that is, the temperature change of multiple shape memory alloys 512 can be controlled by a temperature control element 513. The number and arrangement of the temperature control unit 513 is adjusted according to the arrangement of multiple shape memory alloys 512.

The ways in which the two ends of the shape memory alloy 512 are respectively connected to the pair of clamping arms 511 include, but not limited to, that the shape memory alloy 512 is arranged between the pair of clamping arms 511 with two ends respectively connected to two face-to-face sides of the clamping arms 511. Or the shape memory alloy 512 is arranged at the same side of the pair of clamping arms 511 with two ends respectively connected to the sides of the clamping arms 511 facing the shape memory alloy 512. Or the shape memory alloy 512 is arranged at the same side of the pair of clamping arms 511 with two ends respectively connected to two reverse sides of the clamping arms 511 by connecting pieces. Therefore, the shape memory alloy 512 can still drive the pair of clamping arms 511 to move towards or away from each other in the case of length change.

When temperature is lower than a shape restoration threshold, the shape memory alloy 512 has a first shape state and the distance between the clamping arms 511 is a first distance, and when the temperature is higher than the shape restoration threshold, the shape memory alloy 512 has a second shape state and a distance between the clamping arms 511 is a second distance. The first distance is less than or greater than the second distance. The small one in the first distance and the second distance is configured for the sampling tube 43 clamped by the clamping arms 511, and the larger one is configured for the sampling tube 43 unclamped by the clamping arms 511.

In one embodiment, the temperature control element 513 is a heating element, and the first distance is less than second distance. When the temperature is lower than the shape restoration threshold, the shape memory alloy 512 is in a compressed, or curved, or wavy first shape state, the first distance between the pair of clamping arms 511 is shorter to clamp the sampling tube 43, and the sampling tube 43 is in a blocked state. When the heating element is turned on to heat the shape memory alloy 512 such that the temperature of the shape memory alloy 512 rises above the shape restoration threshold, the shape memory alloy 512 restores the elongated second shape state while driving the pair of clamping arms 511 to move backwards to unclamp the sampling tube 43 and make liquid to flow through the sampling tube 43. When the heating element is turned off and the temperature of the shape memory alloy 512 drops below the shape restoration threshold, the shape memory alloy 512 restores to the first shape state due to two-way shape-memory effect to drive the pair of clamping arms 511 to move towards each other and clamp the sampling tube 43 so that liquid cannot flow through the sampling tube 43.

In another embodiment, the temperature control element 513 is a cooling element, and the first distance is greater than the second distance. When the temperature is higher than the shape restoration threshold, the shape memory alloy 512 is in a compressed, or curved, or wavy second shape state, the second distance between the pair of clamping arms 511 is shorter to clamp the sampling tube 43, and the sampling tube 43 is in a blocked state. When the cooling element is turned on to cool the shape memory alloy 512 such that the temperature of the shape memory alloy 512 drops below the shape restoration threshold, the shape memory alloy 512 restores the elongated first shape state while driving the pair of clamping arms 511 to move backwards to unclamp the sampling tube 43 and make liquid to flow through the sampling tube 43. When the cooling element is turned off and the temperature of the shape memory alloy 512 rises above the shape restoration threshold, the shape memory alloy 512 restores to the second shape state due to two-way shape-memory effect to drive the pair of clamping arms 511 to move towards each other and clamp the sampling tube 43 so that liquid cannot flow through the sampling tube 43.

The switch assembly 5 further comprises an auxiliary block 56 arranged on the inner wall of the enclosure 1 to limit the pair of clamping arms 511 to move in a straight line, so as to prevent the pair of clamping arms 511 deviation. The auxiliary block 56 can also assist in the installation of other structural members.

In addition, the switch assembly 5 further comprises a sensor 53 and a storage module 54 that communicate with the control unit 52. The sensor 53 is configured to collect physiological parameters and/or images inside GI tract, and the collected information can be used for system positioning to determine the location of the sampling capsule 100 and whether sampling is needed. The storage module 54 is configured to store the physiological parameters and/or images of different regions of a patient's GI tract when they are normal or may have lesions. The control unit 52 can compare the information obtained by the sensor 53 with the stored physiological parameters and/or image information to determine the location of the sampling capsule 100 and whether sampling is needed.

The sensor 53 is at least one of an image sensor, or a pH sensor, or an ultrasonic sensor, and when there are multiple sensors 53, the comparison is more accurate.

When the sensor 53 includes an image sensor, part of the enclosure 1 is transparent, and the image sensor can obtain images of GI tract outside the sampling capsule 100.

When the sensor 53 includes an ultrasonic sensor, the physiological parameters of GI tract are obtained by ultrasonic waves, and the enclosure 1 serves as an acoustic medium between the ultrasonic sensor and the imaged object such as an inner wall of GI tract, and the acoustic performance of the acoustic medium enables it to provide good acoustic coupling effect and improves the quality of ultrasound imaging.

When the sensor 53 includes a pH sensor, the enclosure 1 has a window through which the pH sensor contacts the liquid inside GI tract. It will be understood by those skilled in the art that the window is configured such that the liquid inside GI tract can only have a contact with the measuring part of the pH sensor but having no contact with other components inside the enclosure 1.

The sampling capsule 100 further comprises a wireless transmission module 55 for communicating with an external processing terminal. That is, the wireless transmission module 55 transmits the information collected by the sensor 53 to the external processing terminal which processes the information to more accurately determine the location of the sampling capsule 100 and whether sampling is needed, or the external processing terminal updates the information of the storage and the controller through the wireless transmission module 55. In addition, the information obtained by the sensor 53 can also be displayed in real time, and based on the information, doctor can actively send an instruction to the sampling capsule 100 to start sampling.

In the embodiment, the storage module 54 is further used to store information transmitted by the external processing terminal.

Hereinafter, an embodiment having the wireless transmission module 55 can be taken as an example to explain how the operating state of the sampling capsule 100 is controlled assisted by each sensor 53.

When the sensor 53 is an image sensor, the images obtained by the sensor 53 are transmitted to the external processing terminal through the wireless transmission module 55 for processing. The external processing terminal can process the images based on a visual check by a doctor or a computer vision algorithm, and the location of the sampling capsule 100 inside a patient's GI tract can be identified. In addition, visual check or computer vision algorithm can also identify the presence of some lesions according to the images to determine whether sampling is needed. If sampling is needed, the external processing terminal transmits such need to the control unit 52 through the wireless transmission module 55, and the control unit 52 controls the switch assembly 5 to unclamp the sampling tube 43 to start sampling. Specifically, when a special image is identified or other special information is identified, that is, the sampling requirement is met, the external processing terminal may send a reminder message to the doctor for confirmation, or directly send a sampling command through the wireless transmission module 55 to the sampling capsule 100 to start sampling.

When the sensor 53 is an ultrasonic sensor, the process is similar to the image sensor described above, with the only difference that the images obtained are B-mode ultrasound images, and details are not described herein.

When the sensor 53 is a pH sensor, the obtained pH value is transmitted to the external processing terminal through the wireless transmission module 55 for processing to identify the location of the sampling capsule 100, and thereby determine whether to start sampling. If sampling is needed, the external processing terminal transmits such need to the control unit 52 through the wireless transmission module 55, and the control unit 52 controls the switch assembly 5 to unclamp the sampling tube 43 to start sampling. Specifically, when a special pH value or special pH curve fluctuation is identified, that is, the sampling requirement is met, the external processing terminal may send a reminder message to the doctor for confirmation, or directly send a sampling command through the wireless transmission module 55 to the sampling capsule 100 to start sampling.

The sampling capsule 100 further comprises one or more batteries (not shown) that supply power to each structure of the switch assembly 5, to ensure the control unit 52, the clamping mechanism 51, the wireless transmission module 55, the storage module 54 and the sensor 53 operate normally.

In the embodiment, the number of the inner sample inlets 41 and the outer sample inlets 42 is not limited. Those skilled in the art can understand that "Clamp the sampling tube 43 to make it in a blocked state" means cutting off the passage between all of the inner sample inlets 41 and the outer sample inlets 42.

When the number of the outer sample inlets 42 is at least two, at least two of the outer sample inlets 42 are evenly distributed on the circumference of the enclosure 1, so that the liquid around the sampling capsule 100 inside GI tract can flow into the sample chamber 3, avoiding a failure of sampling caused by the lack of liquid or insufficiency of liquid at a specific position inside GI tract. At least two of the outer sample inlets 42 may also be randomly distributed on the circumference of the enclosure 1.

When the number of the inner sample inlets 41 is at least two, at least two of the inner sample inlets 41 are evenly distributed on the partition wall 2, which ensures a fast sampling and that sample liquid flow into the sample chamber 3 is evenly distributed to avoid an affection on sampling by local accumulation of liquid. At least two of the inner sample inlets 41 may also be randomly distributed on the partition wall 2.

When the number of the inner sample inlets 41 is one and the number of the outer sample inlets 42 is at least two, the inner sample inlet 41 is connected to all of the outer sample inlets 42 by the sampling tube 43. In particular, the sampling tube 43 comprises an axial tube 431 extending axially along the sampling capsule 100 and connecting to the inner sample inlet 41, and a radial tube 432 extending radially along the sampling capsule 100 and connecting to each of the outer sample inlets 42. In an example, wherein one inner sample inlet 41 and two outer sample inlets 42 are comprised, the sampling tube 43 is T-shaped and comprises an axial tube 431 and two radial tubes 432.

Preferably, the inner inlet 41 and all of the outer sample inlets 42 can be blocked or unblocked by clamping or unclamping the axial tube 431 by a switch assembly 5. Also, the switch assembly 5 can clamp or unclamp the radial tube 432, in which case the number of the switch assemblies 5 is the same as the number of the radial tubes 432. Or, only one switch assembly 5 is configured, but the switch assembly 5 comprises pair(s) of clamping arms 511 which have the same number as the radial tubes 432, and the number of temperature control elements is increased or decreased, as the case may be.

When the number of the inner sample inlets 41 is at least two and the number of the outer sample inlets 42 is at least two, all of the inner sample inlets 41 can be connected to all of the outer sample inlets 42 by a sampling tube 43. In particular, the sampling tube 43 includes axial tubes 431 extending axially along the sampling capsule 100 and connecting to at least two of the inner sample inlets 41 one by one, and radial tubes 432 extending radially along the sampling capsule 100 and connecting to each of the outer sample inlets 42 one by one. In an example, wherein two inner sample inlets 41 and two outer sample inlets 42 are comprised, the sampling tube 43 comprises two axial tubes 431 and two radial tubes 432.

Due to the complexity of arrangement of the axial tube 431 or the radial tube 432, the switch assemblies 5 of the same number as the axial tubes 431 can be configured to clamp or unclamp the axial tubes 431, or the switch assemblies 5 of the same number as the radial tubes 432 can be configured to clamp or unclamp the radial tubes 432. Alternatively, one switch assembly 5 can be configured to clamp or unclamp all of the axial tubes 431, wherein the switch assembly 5 comprises pair(s) of clamping arms 511 which have the same number as the axial tubes 431, and the number of temperature control elements is increased or decreased as the case may be. Or one switch assembly 5 can be configured to clamp or unclamp all of the radial tubes 432, wherein the switch assembly 5 comprises pair(s) of clamping arms 511 which have the same number as the radial tubes 432, and the number of temperature control elements is increased or decreased as the case may be.

When the number of the inner sample inlets 41 is at least two and the number of the outer sample inlets 42 is at least two, multiple sampling tubes 43 described above can be configured to connect all of the inner sample inlets 41 and the outer sample inlets 42, and each of the sampling tubes 43 connects at least one of the inner sample inlets 41 and at least one of the outer sample inlets 42. In an example, wherein two inner sample inlets 41 and two outer inlets 42 are comprised, two separate sampling tubes 43 can be configured to connect all of the inlets, wherein one end of each of the sampling tubes 43 connects one inner sample inlet 41 and another end connects one outer sample inlet 42. When the number of the inner sample inlets 41 is inconsistent with the number of the outer sample inlets 42, the sum of the axial tubes 431 of multiple separate sampling tubes 43 is consistent with the inner sample inlets 41, and the sum of the radial tubes 432 of multiple separate sampling tubes 43 is consistent with the outer sample inlets 42. In this embodiment, the specific structure of each of the sampling tubes 43 and the arrangement of the switch assembly 5 thereof are similar with the above embodiment, and details are not described herein again.

The present invention further provides a sampling capsule system comprising any kind of the sampling capsules 100 as described above and an external processing terminal in communication with a switch assembly 5. Specifically, the switch assembly 5 comprises a control unit 52 that controls operating state of the switch assembly 5, and a wireless transmission module 55 that communicates with the control unit 52. The external processing terminal communicates with the control unit 52 through the wireless transmission module 55 to control the operating state of the sampling capsule 100. Other structures are as described above and are not described again.

The present invention further provides a control method based on the sampling capsule 100 described above, comprising the steps of: determining whether sampling is needed, and if sampling is needed, the switch assembly 5 unclamps the sampling tube 43, and after sampling ends, the switch assembly 5 clamps the sampling tube 43. To determine whether sampling is needed, any one of the methods as described above can be used, and details are not described herein again. Any one of the methods as described above can be used for the switch assembly 5 to clamp or unclamp the sampling tube 43, and details are not described herein again.

To sum up, the sampling capsule 100 sucks sample liquid into the sample chamber 3 through outer sample inlet 42, sampling tube 43 and inner sample inlet 41 when the capsule reaches the region of interest inside a patient's GI tract. The switch assembly 5 unclamps the sampling tube 43 allowing liquid to flow through. When sampling ends, the switch assembly 5 tightly clamps the sampling tube 43 to prevent sample leak or contamination. The switch assembly 5 can control the unblocking time of the sampling tube 43 to precisely control the volume of sample sucked into the sample chamber 3. In addition, the switch assembly 5 actively controls the unclamping or clamping of the sampling tube 43 to make the sampling capsule 100 free to suck sample liquid at any position inside a GI tract without being affected by the environment therein. Therefore, the sampling capsule 100 has a high versatility.

It should be understood that, although the specification is described in terms of embodiments, not every embodiment merely includes an independent technical solution. Those skilled in the art should have the specification as a whole, and the technical solutions in each embodiment may also be combined as appropriate to form other embodiments that can be understood by those skilled in the art.

The present invention by no means is limited to the preferred embodiments described above. On the contrary, many modifications and variations are possible within the scope of the appended claims.

What is claimed is:

1. A sampling capsule, comprising:
an enclosure, a partition wall arranged in the enclosure, a sample chamber enclosed by the partition wall and the enclosure at a first side of the partition wall;
and further comprising
an inner sample inlet on the partition wall;
at least two outer sample inlets on the enclosure at a second side of the partition wall;
a sampling tube connecting the at least two outer sample inlets and the inner sample inlet; and
a switch assembly that clamps or unclamps a portion of the sampling tube,
wherein the sampling tube comprises an axial tube and a radial tube, the axial tube extending axially along the sampling capsule and connecting to the inner sample inlet, and the radial tube extending radially along the sampling capsule, and connecting to the at least two outer sample inlets, wherein the axial tube is clamped or unclamped by the switch assembly, or the radial tube is clamped or unclamped by the switch assembly.

2. The sampling capsule of claim 1, wherein the switch assembly comprises a clamping mechanism that clamps or unclamps the portion of the sampling tube, and a control unit that communicates with the clamping mechanism.

3. The sampling capsule of claim 2, wherein the clamping mechanism comprises a pair of clamping arms respectively arranged at two sides of the sampling tube, a shape memory alloy with its two ends respectively connected to the pair of clamping arms to drive the clamping arms to move towards or away from each other, and a temperature control element for controlling a temperature of the shape memory alloy, wherein the temperature control element is in communication with the control unit;
wherein the shape memory alloy has a first shape state and a distance between the clamping arms is a first distance when the temperature is lower than a shape restoration threshold;
wherein the shape memory alloy has a second shape state and another distance between the clamping arms is a second distance when the temperature is higher than the shape restoration threshold; and
wherein the first distance is less than or greater than the second distance, and between the first distance and the second distance, the smaller distance is configured for the sampling tube to be clamped by the clamping arms, and the larger distance is configured for the sampling tube to be unclamped by the clamping arms.

4. The sampling capsule of claim 3, wherein the temperature control element is a heating element, and the first distance is less than the second distance.

5. The sampling capsule of claim 3, wherein the temperature control element is a cooling element, and the first distance is greater than the second distance.

6. The sampling capsule of claim 3, wherein
the shape memory alloy is arranged between the pair of clamping arms with the two ends respectively connected to two face-to-face sides of the clamping arms; or the shape memory alloy is arranged at a same side of the pair of clamping arms with the two ends respectively connected to two reverse sides of the clamping arms by connecting pieces; or
the shape memory alloy is arranged at the same side of the pair of clamping arms with the two ends respectively connected to another side of the clamping arms facing the shape memory alloy.

7. The sampling capsule of claim 3, wherein the pair of clamping arms correspond to the shape memory alloy, or multiple pairs of clamping arms correspond to the shape memory alloy.

8. The sampling capsule of claim 3, wherein the shape memory alloy corresponds to the temperature control element, or multiple of the shape memory alloys correspond to the temperature control element.

9. The sampling capsule of claim 3, wherein the switch assembly further comprises an auxiliary block arranged on an inner wall of the enclosure to limit the pair of clamping arms from moving in a straight line.

10. The sampling capsule of claim 2, wherein the switch assembly further comprises:
a sensor communicating with the control unit, wherein the sensor collects physiological parameters and/or images inside a patient's GI tract, and
a storage module communicating with the control unit, wherein the storage module stores the physiological parameters and/or the images of different regions of the patient's GI tract when they have or do not have lesions.

11. The sampling capsule of claim 10, wherein the sensor is selected from an image sensor, a pH sensor, or an ultrasonic sensor.

12. The sampling capsule of claim 11, wherein the sampling capsule comprises the image sensor, and part of the enclosure is transparent.

13. The sampling capsule of claim 11, wherein the sampling capsule comprises the pH sensor, and the enclosure has a window through which the pH sensor contacts liquid inside the patient's GI tract.

14. The sampling capsule of claim 10, wherein the sampling capsule further comprises a wireless transmission module for communicating with an external processing terminal.

15. The sampling capsule of claim 1, wherein a number of the inner sample inlets is one.

16. The sampling capsule of claim 1, wherein a number of the inner sample inlets is at least two, multiple sampling tubes connect all of the inner sample inlets and the outer sample inlets, and each of the multiple sampling tubes connects at least one of the inner sample inlets and at least one of the outer sample inlets.

17. The sampling capsule of claim 1, wherein the sampling capsule further comprises a releasing port on the enclosure on the first side of the partition wall and being connected to the sample chamber to obtain a sample liquid.

18. A sampling capsule system, comprising the sampling capsule of claim 1, and an external processing terminal that is in communication with the switch assembly.

19. The sampling capsule system of claim 18, wherein the switch assembly comprises a control unit that controls an operating state of the switch assembly, and a wireless transmission module that communicates with the control unit, wherein the external processing terminal communicates with the control unit through the wireless transmission module.

* * * * *